United States Patent [19]

Wainwright et al.

[11] 4,366,260

[45] Dec. 28, 1982

[54] CATALYSTS FOR METHANOL SYNTHESIS

[75] Inventors: Mark S. Wainwright, Randwick; Warwich L. Marsden, North Sydney; Jan B. Friedrich, Asquith, all of Australia

[73] Assignee: Unisearch Limited, Kensington, Australia

[21] Appl. No.: 296,222

[22] Filed: Aug. 25, 1981

Related U.S. Application Data

[62] Division of Ser. No. 213,542, Dec. 5, 1980.

[30] Foreign Application Priority Data

Dec. 17, 1979 [AU] Australia ............................ PE1743

[51] Int. Cl.$^3$ ................. C07C 27/06; C07C 31/04
[52] U.S. Cl. ........................... 518/713; 252/463
[58] Field of Search .................................. 518/713

[56] References Cited

U.S. PATENT DOCUMENTS 2,061,470 11/1936 Larson ................................ 518/713
3,850,850 11/1974 Collins ............................... 518/713

FOREIGN PATENT DOCUMENTS 1389709 4/1975 United Kingdom ............... 518/713

*Primary Examiner*—Howard T. Mars
*Attorney, Agent, or Firm*—Michael J. Striker

[57] ABSTRACT

A method for the preparation of a low temperature catalyst suitable to synthesize methanol or mixtures of methanol and dimethyl ether, comprising forming an alloy containing 35 to 60%, preferably 44 to 50%, by weight of aluminium, 0.1 to 25%, preferably 13 to 17%, by weight of zinc and the remainder being substantially all copper and extracting the alloy with an aqueous solution of an alkali metal hydroxide, preferably sodium hydroxide, preferably at atmospheric pressure and a temperature of from 50° to 80° C., preferably from 65° to 75° C.

The resultant novel catalyst is used to produce methanol or a mixture of methanol and dimethyl ether by a process comprising contacting the catalyst with a gaseous mixture of carbon monoxide or carbon dioxide, or a mixture thereof, with hydrogen. This reaction is preferably carried out at a temperature of from 200° to 290° C. and a pressure of from 1500 to 7500 kPa and linear hourly space times of from 0.001 to 0.5 hours.

3 Claims, 6 Drawing Figures

CATALYSTS FOR METHANOL SYNTHESIS

There is a division of application Ser. No. 213,542, filed Dec. 5, 1980.

The present invention relates to a low temperature methanol synthesis catalyst and to a process for the production of methanol from gaseous mixtures of carbon monoxide or carbon dioxide or mixtures thereof and hydrogen.

Although the first patent for methanol synthesis on copper based catalysts was filed as early as 1921 by Patart (Haynes, "American Chemical Industry—a History" P. 169 (1948)), these catalysts were not used commercially for almost half a century due to the low thermal resistance of copper and its susceptibility to sulphur poisoning.

Interest in copper-based catalysts was revived when ICI developed a process for producing synthesis gas relatively free of impurities by steam reforming of naphtha (Humphreys et al., Chem. Econ. Eng. Rev. 6, 26 (1974)). This led to the development by ICI in the late 1960's of the modern low pressure, low temperature methanol synthesis process. Parallel to the development by ICI was the development of further gas purification processes, such as the Lurgi Rectisol process (Supp, Chem. Tech. 3,430 (1973)), so that now synthesis gas essentially free of sulphur can be produced from coal as well as natural gas and crude oil.

The modern ICI methanol process was initially based on ternary catalysts containing copper oxide (which was reduced in situ), zinc oxide and chromic oxide (U.S. Pat. No. 3,326,956), and the conditions used were in the order of 250° to 270° C. and 5,000 to 10,000 kPa. Further research has shown that if alumina is used in place of chromic oxide longer catalyst life results, and so most low pressure catalysts now contain alumina rather than chromic oxide as the third component (U.S. Pat. No. 3,790,505). These catalysts are produced by coprecipitation of soluble zinc and copper salts (usually the nitrates) with an alkali carbonate solution. The resulting mixture of carbonates is heated to form a mixture of oxides which are then mixed with aluminium oxide.

Further improvements in methanol production will be made by the development of catalysts that have higher intrinsic activity, selectivity, thermal stability and resistance to poisoning. This specification describes the preparation of a novel range of zinc promoted Raney copper catalysts which have been shown to have acceptable levels of activity and stability.

The present invention consists in a low temperature methanol synthesis catalysts composition suitable to synthesise methanol, or mixtures of methanol and dimethyl ether, by the reaction of carbon monoxide or carbon dioxide or mixtures thereof with hydrogen, said catalyst composition being prepared from an alloy containing from 35 to 60% by weight of aluminium, 0.1 to 25% by weight of zinc, and the remainder being substantially all copper, by extraction with an aqueous solution of an alkali metal hydroxide.

In another aspect the present invention consists in a method for the production of methanol, or mixtures of methane and dimethyl ether, comprising contacting a gaseous mixture of carbon monoxide or carbon dioxide, or a mixture thereof, with hydrogen, with a catalyst prepared by the extraction of an alloy comprising from 35 to 60% by weight of aluminium, 0.1 to 25% by weight of zinc, and the remainder being substantially all copper, with an aqueous solution of an alkali metal hydroxide.

In a still further aspect the present invention consists in a method for the production of a low temperature methanol synthesis catalyst composition suitable to synthesise methanol, or mixtures of methanol and dimethyl ether, by the reaction of carbon monoxide or carbon dioxide or mixtures thereof with hydrogen, comprising forming an alloy containing from 35 to 60% by weight of aluminium, from 0.1 to 25% by weight of zinc, and the remainder being substantially all copper and extracting the alloy with an aqueous solution of an alkali metal hydroxide.

The catalyst composition is preferably prepared from an alloy which contains from 7 to 20% by weight of zinc and most preferably from 13 to 17% by weight thereof. The alloy also preferably has a copper content of from 30 to 43% by weight, and most preferably of from 33 to 37% by weight, and an aluminium content of from 44 to 50% by weight, most preferably 47%. The extraction of the aluminium from the alloy using an aqueous solution of an alkali metal hydroxide is known as the Raney Process and has been used previously for the production of nickel and copper catalysts for certain hydrogenation reactions though not for the production of methanol.

The catalyst preferably has a particle size in the range from 200 microns to 3 cms.

The alkali metal hydroxide used in the extraction is for commercial reasons preferably sodium hydroxide or potassium hydroxide, most preferably sodium hydroxide at a concentration in an aqueous solution of 20% by weight. The alkali metal hydroxide solution is preferably added in an excess over that required for complete leaching of the aluminium present.

The leaching is preferably conducted at atmospheric pressure and at a temperature of from ambient temperature up to the boiling point of the alkali solution. The temperature is preferably between 50° and 80° C. and most preferably between 65° and 75° C. If it is desired to produce mixtures of methanol and dimethyl ether the extraction conditions should be made less severe by using slightly less caustic solution than is required from complete solution of the aluminium and using caustic solutions of less than 20% by weight. It is believed that the use of these latter conditions results in particles of alumina being deposited on the surface of the copper and that these particles of alumina act as a catalyst for the dehydration reaction in which two methanol molecules are converted to a molecule of dimethyl ether and a molecule of water.

The process according to this invention is preferably conducted at a temperature of from 200° C. to 290° C. and at pressures of from 1500 to 7500 kPa, however as will be discussed hereinafter pressure differences can result in the production of greater or lesser amounts of dimethyl ether. Linear hourly space times (LHST) of between 0.001 and 0.5 hours are preferred, however, longer reaction times have been found to favour dimethyl ether production over methanol production.

Hereinafter given are examples illustrating the present invention.

EXPERIMENTAL

Figure 1:
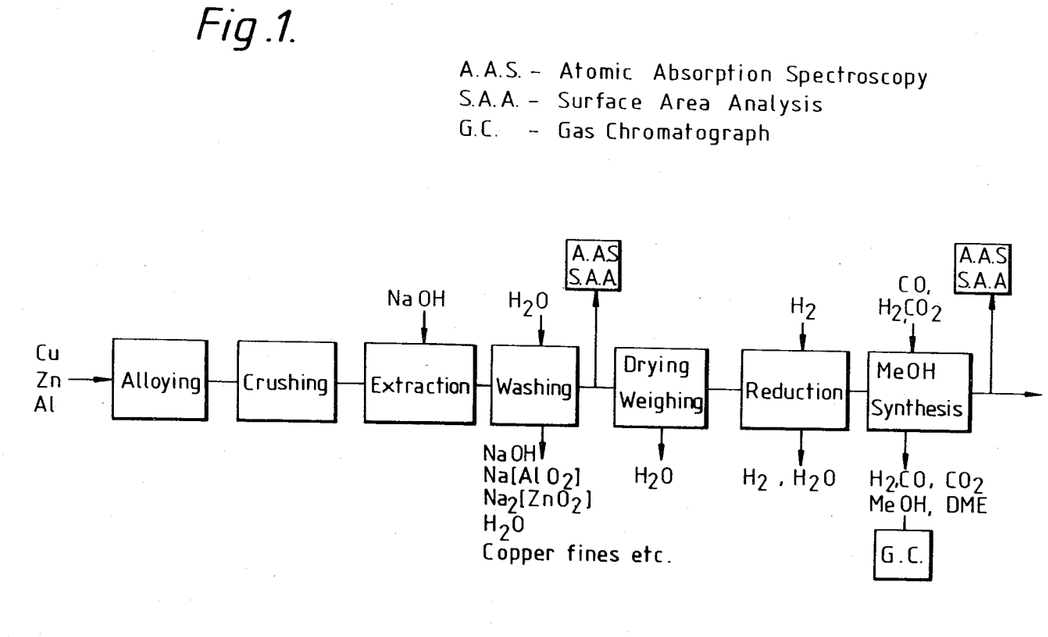

FIG. 1 shows a flow diagram of the procedures used in catalyst preparation and characterization.

Catalyst Preparation

All of the Raney catalysts were prepared from eight alloys containing nominally 50 wt.% aluminium and varying amounts of copper and zinc.

Alloys were prepared from high purity metal (Al>99.9%, Zn>99.8%, Cu>99.5%). The composition of the alloys are given in Table 1. The 50 wt.% Al was used since it corresponded to the composition $CuAl_2$ in the Raney copper. $CuAl_2$ is known to be the leachable phase (Nadirov et al., Z Fiz. Khim, 51, 1422 (1977)). The alloys were prepared in carbon crucibles heated in an induction furnace. Alloy samples of between 200 and 400 g were prepared in each bath.

Copper, having the highest melting point, was melted first and then aluminium was added. After vigorous stirring with a carbon rod the metal was cooled to below the boiling point of zinc before that metal was added with stirring. The melt was then rapidly quenched in cold water. The resulting alloy samples were crushed in a jaw crusher and screened. The aluminium-zinc alloy was cooled in liquid nitrogen in order to make it sufficiently brittle to crush.

Catalysts were prepared from the alloys by a method similar to that adopted in a previous study using Raney Nickel alloys (Freel et al. Journal of Catalysts 14,247 (1969)). After an extraction period of two hours the catalyst was washed with distilled water at 25° C. first by decantation and finally by water flow until the pH of the wash water was 7. The catalyst was then screened under water to remove any particles passing through a 45 mesh screen. The catalysts were stored under distilled water in stoppered vessels prior to use. Specific differences in extraction procedures are discussed later in this specification.

Catalyst Characterization

Acid digests of the alloys and catalysts were analysed for aluminium zinc and copper content by atomic absorption spectroscopy. Compositions of alloys and catalysts are given in Table 1.

The surface areas of catalysts were measured by nitrogen absorption at −196° C. using a Micromeritics 2200 High Speed surface area analyzer. The specific surface areas are given in Table 1.

Reaction Apparatus and Procedure

Experiments to measure catalyst activity and selectivity were performed in conventional flow reactors. A tubular reactor, constructed from 12.7 mm O.D. seamless copper tubing, was used in the experiments performed with catalysts 1 through 6. All further experiments were conducted in a U-tube reactor constructed from 9.7 mm O.D. seamless copper tubing. Experiments showed that the empty reactors had no catalytic activity. The reactors were immersed in vigorously stirred, molten salt baths in order to obtain quasi-isothermal reaction conditions. The temperature of the bath was controlled to +0.5° C. using a PID controller.

Pre-mixed gases containing $CO/H_2$ and $CO/CO_2/H_2$ (Commonwealth Industrial Gases Ltd.) were fed from high pressure cylinders to the reactor via a needle valve. The exact compositions of the feed gases were determined by gas chromatography and confirmed using an Anarad Model AR-600R $CO/CO_2$ infrared gas analyzer. The pressure in the reactor was controlled using a back pressure regulator and was measured by a Bourdon gauge. The flowrate of the exit gases were measured using a wet gas meter.

The composition of the reactor effluent was determined by gas chromatography. A Gowmac model 552 gas chromatograph equipped with a thermal conductivity detector was employed. A Porapak T column (3 m×6.3 mm O.D. Aluminium), operated isothermally at 150° C., gave excellent separation of CO, $CO_2$, dimethyl ether, water and methanol. Hydrogen was employed as carrier gas and hence was not detected in the reactor effluent. Peak areas were measured using a Spectra-Physics Mirigrator electronic integrator. The thermal conductivity detector was calibrated daily using a gravimetric standard mixture containing $CO,CO_2$ and dimethyl ether in hydrogen (Commonwealth Industrial Gases Ltd.).

The range of experimental conditions employed was chosen to represent those in industrial reactors employing low temperature methanol synthesis catalysts. In most experiments the hydrogenation reactions were conducted at 275° C. and 5500 kPa. Other conditions employed are mentioned later in the specification.

RESULTS

Comparison of catalyst properties is made on the basis of the nominal compositions of the starting alloys. The various properties are discussed under separate headings below. Catalyst properties are summarized in Table 1.

Specific Surface Areas of Catalysts

From the results in Table 1 it can be seen that the specific surface area increased with zinc content of the alloys up to 17 wt.% zinc. It should be noted that the extraction procedures adopted in this work were not isothermal and could lead to variations in surface areas of catalysts.

Activity of Catalysts

Figure 2:
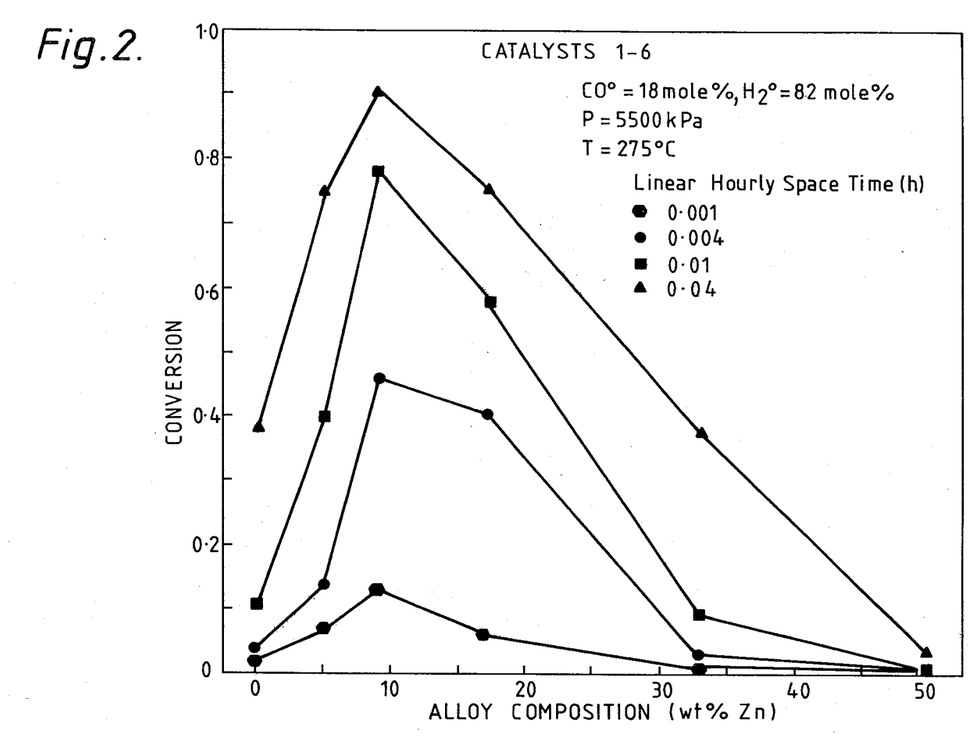

The overall activity of a catalyst was measured by its ability to convert carbon monoxide to products including methanol, dimethyl ether and carbon dioxide. FIG. 2 shows the conversion of carbon monoxide plotted against alloy composition for catalysts 1 through 6 at various space times. The curves shows an apparent maximum in activity for catalysts prepared from an alloy containing 50; wt.% aluminium with 33–43 wt.% copper and 7–17 wt.% zinc.

Selectivity of Catalysts

The results for the hydrogenation of carbon monoxide over catalyst 1 through 6 showed high selectivity to methanol; at low space times for catalysts 1, 2, 3 and 6 containing low zinc levels. However, this selectivity decreased with increasing zinc content for catalyst 4 and 5.

Figure 3:
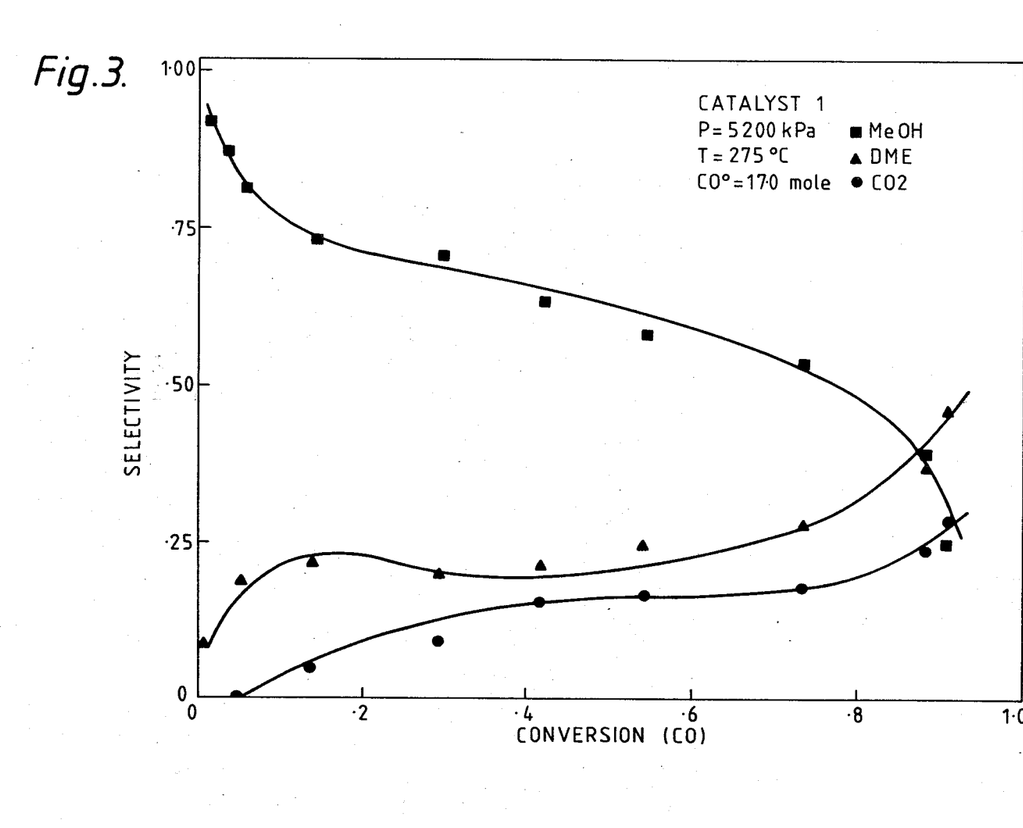
Figure 4:
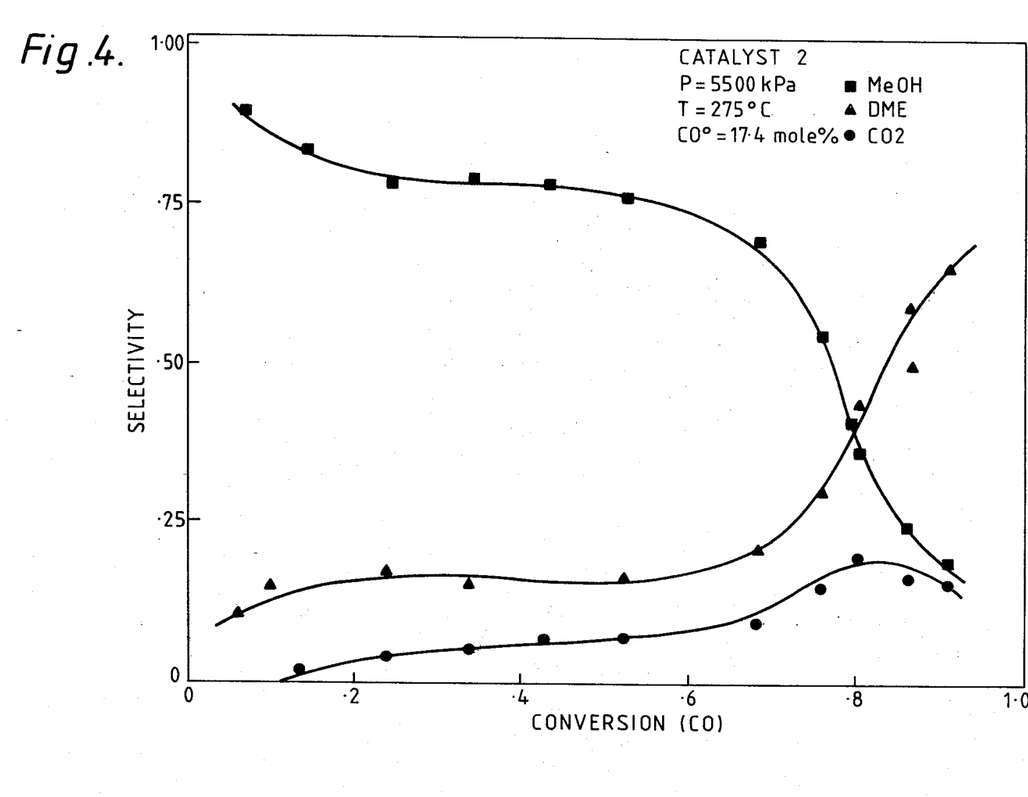
Figure 5:
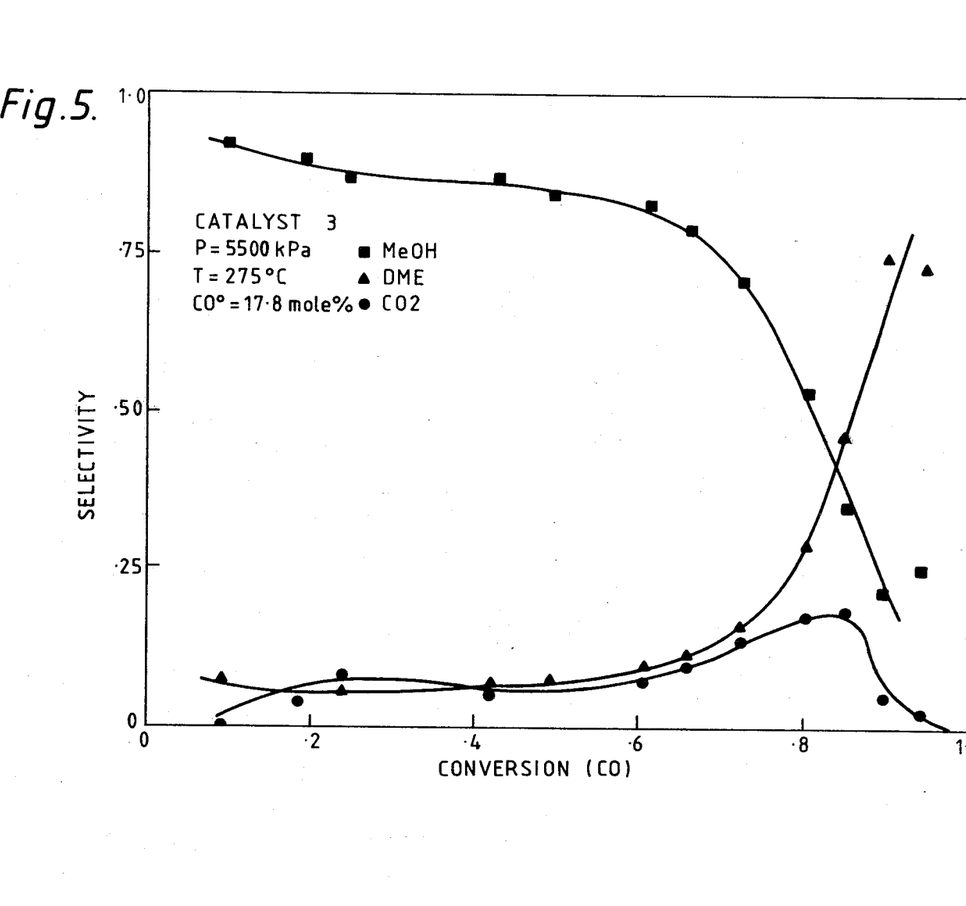

The selectivities of catalysts 1, 2 and 3 are plotted against conversion of carbon monoxide in FIGS. 3, 4 and 5 respectively. In these plots the selectivity to methanol is seen to drop sharply at low conversions for catalyst 1 and less sharply for catalyst 2. In the case of catalyst 3 the decrease in selectivity with conversion is very small. A similar trend was observed in the hydrogenation of a mixure of carbon monoxide and carbon dioxide.

The selectivity to dimethyl ether is seen to mirror the shape of the methanol selectivity curves in FIGS. 3, 4 and 5. This indicates that dimethyl ether is formed from methanol by a dehydration reaction $$2CH_3OH \rightleftharpoons CH_3OCH_3 + H_2O \quad (1)$$

When a mixture of carbon monoxide and carbon dioxide was hydrogenated the selectivity to dimethyl ether was reduced.

The selectivity to carbon dioxide decreased with increased zinc content for catalysts 1 to 3. This indicates that the carbon dioxide is produced by the shift reaction $$CO + H_2O \rightleftharpoons CO_2 + H_2 \quad (2)$$

through water produced by the dehydration reaction (equation (1)).

Rate of Methanol Production

A comparison of methanol production rates between the zinc-promoted Raney copper catalysts in the optimal composition range and those of the industrial catalyst is made in Table 2. It can be seen that catalysts 3 and 6 have activities, (expressed as $cm^3$ of liquid methanol produced per $cm^3$ of catalyst) comparable to the industrial catalyst under similar reaction conditions.

Extraction Procedures

The extraction of aluminium alloys to produce Raney catalysts is a complex procedure with many variables including caustic concentration, rate of caustic addition and temperature being among the most important. The process is even more complex when a second leachable component such as zinc is included in the alloy system. Preliminary experiments to determine the effects of temperature and caustic addition were made with two alloys having composition in the optimum range. As with the extraction of alloys 1 to 6, caustic was added in a 200% excess of that required for complete leaching of the aluminium present. The extraction procedures and temperatures of extraction are summarized in Table 3. The temperature of extraction is divided into two parts. The first refers to the temperature of the water bath in which the extraction vessel was placed. The other refers to the temperature rise within the extraction mixture. From Table 1 it can be seen that no clear relationship exists between the conditions of extraction and the surface area of the catalyst prior to use in the reactor.

The conditions of extraction have a marked effect on catalyst activity and selectivity as can be seen in Table 4. harsh conditions of extraction produce catalysts with high activity and selectivity for methanol production (catalysts 8, 9 and 10). Whereas catalysts produced by milder extraction of the same alloys had low activities and high selectivities to dimethyl ether formation.

Effect of Temperature and Pressure

Initially experiments were conducted on catalyst 3 to determine the influence of temperature and pressure on the hydrogenation of carbon monoxide. The catalyst showed little activity below 240° C. The influence of pressure was small between 2750 (400 psi) and 4130 (600 psi) kPa at all temperatures between 225° and 290° C. However, at higher pressures the rate increased rapidly with pressure. These observations are similar to those observed elsewhere (Schermuly and Luft, 1977), for the hydrogenation of $CO/CO_2$ mixtures of similar composition over an industrial copper-based catalyst. All further experiments were conducted at 275° C. and 5500 kPa.

DISCUSSION

The results presented above indicate that Raney-type catalysts produced by the extraction of aluminium-copper-size alloys exhibit high activity for methanol production, an optimal zinc content between 7 and 17 wt.% has been shown for the extraction conditions used. The major points for discussion of the results of this investigation are the activities of these catalysts and the selectivities to methanol and dimethyl ether.

In the absence of knowledge as to the exact surface composition of these catalysts it is only possible to postulate tentative reasons for the selectivity and activity results and are given by way of possible explanation only and the claims attached hereto are not to be limited by reference to the following explanation. The activity and selectivity to methanol found in catalyst 1 indicate that copper is an active catalyst for methanol synthesis. The enhancement in activity and selectivity seen in catalysts made from alloys containing up to 20 wt.% zinc may result from either an increase in specific surface area caused by caustic attack on zinc, as well as the aluminium or by a change in the electronic nature of the copper surface.

Figure 6:
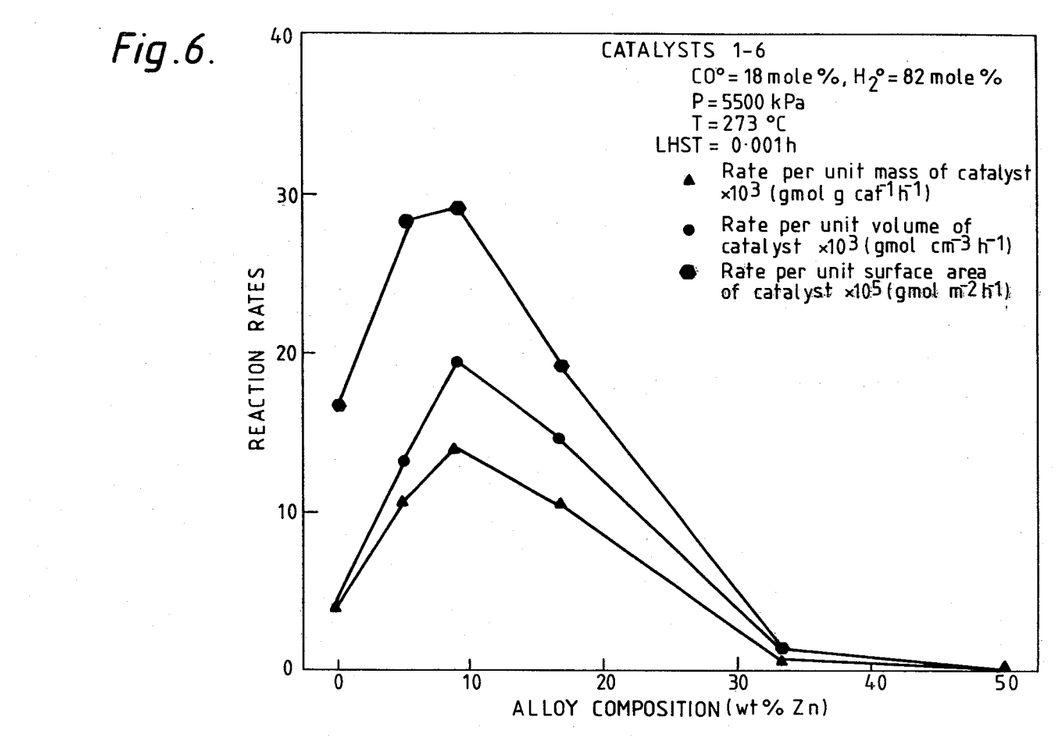

The argument that the inclusion of zinc in the alloy simply produces Raney copper of higher surface area is refuted by the results presented in FIG. 6 where activities are plotted on the basis of unit mass, unit volume and unit surface area. Should the only role of zinc be to produce copper of higher surface area then the activity per unit area should be the same for catalysts containing 0 to 20% zinc. This is obviously not so and therefore the conclusion must be drawn that the residual zinc does promote catalyst activity. In fact, on all three bases on optimum is shown to exist.

However, catalysts containing high zinc levels are shown to have little activity for methanol synthesis. This adds further evidence to the reasoning that the role of zinc is as a promotor rather than the active component in methanol synthesis.

The role of γ-alumina in methanol synthesis was examined by passing a $CO/CO_2/H_2$ synthesis gas mixture over a bed of γ-alumina catalyst particles (Harshaw Chemical Company) at 275° C. and 5500 kPa. At space times between 0.004 and 0.5 h no reaction products were observed. Therefore it is concluded that alumina has no direct role in the hydrogenation of carbon monoxide.

Most of the catalysts produced significant quantities of dimethyl ether, particularly at long contact times. The dimethyl ether is doubtless formed by the dehydration of methanol on an active form of alumina. Until recently alumina has been considered an undesireable component in methanol synthesis catalysts because it does cause the formation of byproduct dimethyl ether. However modern formulations include an inactive form of alumina to provide thermal stability in the catalyts. In this study dimethyl ether was only produced at long contact times on catalysts of near optimum composition. This indicates that the amount of active alumina is small and/or the rate of the dehydration reaction is slow compared with methanol synthesis. It was also found that dimethyl ether formation was reduced by operating at higher pressures.

Dimethyl ether is an undesirable byproduct in methanol synthesis when methanol is desired as a solvent on chemical feedstock. However, it is an intermediate in the production of gasoline from methanol via the Mobil process. In fact in the fixed bed laboratory process Mobil have used a preliminary bed of dehydration catalyst (presumably $\gamma Al_2O_3$) to form an equilibrium dimethyl ether/methanol mixture to feed to the fixed bed of ZSM-5 catalyst to produce gasoline. A recent U.S. Pat. No. 4,011,275 claims the use of a fixed bed of mixed methanol synthesis catalyst and dehydration catalyst to produce a mixture of methanol and dimethyl ether from synthesis gas. An earlier U.S. Pat. No. 3,894,102 claims the use of a 1:1 mixture of a copper (methanol synthesis) catalyst and alumina (acidic dehydration) catalyst to produce dimethyl ether from synthesis gas. The catalysts according to this invention are capable of producing both methanol and dimethyl ether in varying quantities depending on the conditions of reaction (contact time and pressure) and method of extracting the alloy.

From the results presented in Tables 3 and 4 it is apparent that the conditions of extraction are most important in determining catalyst activity and selectivity. Mild extraction conditions produce catalysts of low activity and high selectivity to dimethyl ether formation. This is most likely due to the formation of larger amounts of surface alumina under these conditions. This alumina is active for dehydration but totally inactive for methanol synthesis.

Of considerable importance in the development of catalysts for methanol synthesis is catalyst stability. Catalysts were employed over a period of several weeks with no apparent loss in activity when $CO/CO_2/H_2$ mixtures were employed. However, a linear decay in activity was noted when no $CO_2$ was present in the synthesis gas. Typically, one catalyst of near optimum composition exhibited a linear loss in activity to 80% of the original activity after 260 hours of continuous operation at 275° C.

The influence of $CO_2$ in the synthesis gas for the Raney catalysts was similar to that for the industrial catalyst. In general, the presence of as little as 2% $CO_2$ gave a three fold increase in activity, for synthesis gases containing between 12 and 25% CO. The $CO_2$ was not consumed in the reaction under the conditions employed. In the case of synthesis gas containing no CO it was noted that at high space times water produced in the formation of dimethyl ether caused the shift of CO to $CO_2$ and increased the catalyst activity. These findings are in accordance with those of an extensive investigation of methanol synthesis catalysts (Herman et al., 1979) in which a solution of $Cu^I$ in ZnO is concluded to be the active catalyst component. The results of the current study support the view that the principal role of $CO_2$ is to maintain the catalyst in an active state rather than to take place in a direct hydrogenation to methanol.

TABLE 1

Catalyst and Alloy Properties[a]

| Catalyst | Alloy Compositions (wt. %) ||||||  Catalyst Compositions (wt. %) |||||||| Catalyst Properties |||
| | Nominal ||| Analysis ||| Before Use |||| After Use |||| Surface Area $(m^2g^{-1})$ [b] | [c] | Bulk density $(gcm^{-3})$ |
| | Al | Cu | Zn | Al | Cu | Zn | Al | Cu | Zn | Other | Al | Cu | Zn | Other | | | |
| 1 | 50 | 50 | 0 | 47.3 | 52.7 | 0 | 2.9 | 94.9 | 0 | 2.2 | 2.2 | 87.8 | 0 | 10.0 | 20.8 | 22.7 | 1.10 |
| 2 | 50 | 45 | 15 | 47.3 | 48.2 | 4.4 | 4.6 | 89.1 | 2.5 | 3.8 | 6.2 | 88.3 | 2.9 | 2.6 | 42.8 | 37.7 | 1.25 |
| 3 | 50 | 33.3 | 16.7 | 45.6 | 37.6 | 16.8 | — | — | — | — | 10.0 | 61.8 | 16.7 | 11.5 | — | 54.0 | 1.42 |
| 4 | 50 | 16.7 | 33.3 | 47.9 | 16.1 | 36.0 | — | — | — | — | 13.0 | 27.5 | 45.1 | 14.4 | — | 53.0 | 1.44 |
| 5 | 50 | 0 | 50 | 49.1 | 0 | 50.9 | — | — | — | — | 22.0 | 0 | 51.8 | 26.2 | 35.3 | 42.8 | 1.23 |
| 6 | 50 | 41 | 9 | 50.1 | 38.9 | 11.0 | 11.7 | 64.7 | 10.1 | 13.5 | 12.4 | 62.3 | 9.1 | 16.2 | — | 51.8 | 1.29 |
| 7 | 50 | 42 | 8 | 47.5 | 44.6 | 7.9 | 3.8 | 79.9 | 4.7 | 11.7 | — | — | — | — | 51.6 | 64.4 | 1.14 |
| 8 | .... | .... | .... | .... | .... | .... | 3.3 | 86.3 | 2.9 | 7.6 | — | — | — | — | 39.4 | 49.0 | 1.03 |
| 9 | 50 | 40 | 10 | 48.1 | 42.1 | 9.8 | 6.2 | 70.2 | 8.5 | 15.2 | 6.2 | 70.1 | 8.9 | 14.7 | 50.9 | 39.2 | 1.31 |
| 10 | .... | .... | .... | .... | .... | .... | 4.2 | 79.8 | 5.3 | 11.7 | 4.3 | 79.9 | 5.2 | 11.2 | 55.5 | 65.8 | 1.26 |
| 11 | .... | .... | .... | .... | .... | .... | 5.6 | 75.4 | 7.3 | 11.8 | 5.4 | 75.4 | 7.5 | 11.8 | 63.5 | 28.2 | 1.10 |
| 12 | .... | .... | .... | .... | .... | .... | 9.7 | 66.8 | 18.9 | 4.7 | 10.4 | 66.8 | 20.3 | 2.4 | 50.1 | 23.3 | 1.23 |
| Ind[d] | — | — | — | — | — | — | 4.7 | 46.5 | 27.2 | 21.7 | — | — | — | — | 53.3 | 30.7 | 1.11 |

[a] Particle size of catalysts: 35–45 mesh
[b] Before methanol synthesis
[c] After methanol synthesis
[d] United Catalysts Inc. C79-4, Low Temperature Methanol Catalyst
— Not measured

TABLE 2

Rates of Methanol Production over Zinc-Promoted Raney Copper Catalysts and an Industrial Methanol Synthesis Catalyst (a)

| Catalyst | Feed composition (Balance $H_2$) || LHST (h) | $X_{CH_3OH}$ | $\dfrac{S_{CH_3OCH_3}}{S_{CH\,OH}}$ | $\left(\dfrac{cm^3 CH_3OH}{h.cm^3 cat.}\right)$ |
| | CO(mol %) | $CO_2$(mol %) | | | | |
| 3 | 17.8 | 0 | 0.001 | 0.012 | 0.043 | 0.58 |
| 3 | 17.8 | 0 | 0.004 | 0.057 | 0.031 | 0.71 |
| 3 | 17.8 | 0 | 0.010 | 0.109 | 0.052 | 0.54 |
| 3 | 12.9 | 2.01 | 0.001 | 0.036 | 0.006 | 1.77 |
| 3 | 12.9 | 2.01 | 0.004 | 0.093 | 0.017 | 1.16 |
| 3 | 12.9 | 2.01 | 0.010 | 0.113 | 0.024 | 0.56 |
| 6 | 15.9 | 2.33 | 0.001 | 0.023 | 0.043 | 1.15 |
| 6 | 15.9 | 2.33 | 0.004 | 0.054 | 0.080 | 0.67 |
| Industrial | 14.9 | 2.15 | 0.001 | 0.024 | 0 | 1.20 |
| Industrial | 14.9 | 2.15 | 0.004 | 0.065 | 0 | 0.81 |
| Industrial | 20.8 | 1.77 | 0.001 | 0.051 | 0 | 2.51 |

TABLE 2-continued

Rates of Methanol Production over Zinc-Promoted Raney Copper Catalysts and an Industrial Methanol Synthesis Catalyst (a)

| Catalyst | Feed composition (Balance H$_2$) CO(mol %) | CO$_2$(mol %) | LHST (h) | $X_{CH_3OH}$ | $\dfrac{S_{CH_3OCH_3}}{S_{CH_3OH}}$ | $\left(\dfrac{cm^3 CH_3OH}{h.cm^3 cat.}\right)$ |
|---|---|---|---|---|---|---|
| Industrial | 20.8 | 1.77 | 0.004 | 0.072 | 0 | 0.77 |
| Industrial | 20.8 | 1.77 | 0.010 | 0.120 | 0.001 | 0.60 |

(a) Conditions of Reaction: Pressure 5500 kPa; Temperature 275° C.

TABLE 3

Summary of Extraction Conditions

| Catalyst | Method of NaOH Addition | Temperature of Extraction (°C.) | Maximum Temperature Differential (°C.) | Designation of Extraction |
|---|---|---|---|---|
| 1 to 5 | 13 equal additions at 5 minute intervals | 25 | up to 40 | harsh |
| 6 | 13 additions of increasing volumes | 25 | 13-18 | moderate |
| 7 | continuous addition | 45 | 7 | mild |
| 8 | 13 equal additions | 60 | 12 | moderate |
| 9 | 13 equal additions | 25 | 23 | harsh |
| 10 | 13 equal additions | 50 | 18 | very harsh |
| 11 | continuous addition | 50 | 6 | mild |
| 12 | continuous addition | 30 | 6 | very mild |

TABLE 4

Influence of Extraction Conditions on Activity and Selectivity (a)

| Catalyst | Feed Composition (Balance H$_2$) CO(mol %) | CO$_2$(mol %) | Conversion of CO | $\dfrac{S_{CH_3OCH_3}}{S_{CH_3OH}}$ |
|---|---|---|---|---|
| 9 | 20.8 | 1.77 | 0.35 | 0.042 |
| 10 | 20.8 | 1.77 | 0.25 | 0.131 |
| 11 | 20.8 | 1.77 | 0.01 | 1.40 |
| 12 | 20.8 | 1.77 | neg. | 7.13 |
| 7 | 21.7 | 0 | 0.02 | 1.38 |
| 8 | 21.7 | 0 | 0.15 | 0.390 |
| 9 | 21.7 | 0 | 0.21 | 0.148 |

(a) Space time: 0.01 h

Hereinafter given by way of example only is a preferred embodiment of the present invention.

Alloy Preparation 140 g of copper was placed in a carbon crucible and heated by an induction furnace to its melting point. 200 g of aluminium was then added to the molten copper. The alloy melt was then vigorously stirred with a carbon rod. The melt was then allowed to cool to below the boiling point of zinc. 60 g of zinc was then added and the melt was again vigorously stirred. The melt was then rapidly quenched by pouring it into approximately 25 liters of cold water. The resulting alloy was then dried at ambient temperature, crushed in a jaw crusher and screened. Particles having diameters between 500 um to 700 um were used in the extraction procedure.

Catalyst Preparation

A 20 g sample of the alloy was placed in 111 g of distilled water at 50° C. After purging the system with hydrogen 111 g of 40% (w/w) aqueous sodium hydroxide solution as added over a time period of 0.75 h so that the reaction temperature was kept to 50°±2.5° C. The rate of caustic addition is given in Table 5. No means of stirring was provided. The extent of reaction was monitored by measuring the hydrogen evolution with a wet test gas meter. After 4.5 h reaction time had taken place the catalyst pieces were thoroughly washed with distilled water until the pH of the wash water was 7. The catalyst was then sieved through a 45 mesh screen to remove any fine particles that may have been produced through the leaching process. The catalyst was stored under distilled water in a stoppered vessel prior to use.

Results

The B.E.T. surface area of the catalyst is shown in Table 6. The activity of the catalyst under various reaction conditions is also shown in Table 6.

TABLE 5

Rate of Caustic Addition in the Preparation of Raney Copper-Zinc Catalyst.

| Time Minutes | Rate of Caustic Addition (ml/min) | Total Volume Caustic Added (ml) |
|---|---|---|
| 0 | 0 | 0 |
| 5 | 0.2 | 1.0 |
| 10 | 0.2 | 2.0 |
| 15 | 0.5 | 4.5 |
| 20 | 0.5 | 7.0 |
| 25 | 1.0 | 12.0 |
| 30 | 2.0 | 22.0 |
| 35 | 2.0 | 32.0 |
| 40 | 5.0 | 57.0 |
| 45 | Remainder Caustic Added | 81.0 |

TABLE 6

| Surface area and Activity of Raney Catalyst | |
|---|---|
| Surface Area (M$^2$/g) | Rate × 10$^3$ g mol. gcat$^{-1}$ h$^{-1}$ |
| 32.72 | 3.9$^a$ |
| 32.72 | 4.4$^b$ |
| 32.72 | 8.8$^c$ |

$^a$240° C., 2800 kPa, LHST 0.003, CO,CO$_2$,H$_2$:19.5, 5.5, 7.5
$^b$260° C., 5500 kPa, LHST 0.006, CO,CO$_2$,H$_2$:19.5, 5.5, 7.5
$^c$260° C., 5500 kPa, LHST 0.001, CO,CO$_2$,H$_2$:19.5, 5.5, 7.5

We claim:

1. A method for the production of methanol, or a mixture of methanol and dimethyl ether, comprising contacting a gaseous mixture of carbon monoxide or carbon dioxide, or a mixture thereof, with hydrogen, with a catalyst prepared by forming an alloy containing from 35% to 60% by weight of aluminum, from 0.1% to 25% by weight of zinc, and the remainder being substantially all copper, and extracting a substantial proportion of the aluminum content of the alloy with an aqueous solution of an alkali metal hydroxide.

2. A method as claimed in claim 1 in which the gasses are contacted with the catalyst at a temperature between 215° C. and 290° C. at a pressure of from 1500° to 750° Kpa.

3. A method as claimed in claim 1 in which the gasses are contacted with the catalyst for linear hourly space times of from 0.001 to 0.5 hours.

* * * * *